United States Patent
Nadeau

(10) Patent No.: US 9,429,528 B2
(45) Date of Patent: Aug. 30, 2016

(54) DETERMINING GAS ABSORPTION LINE FROM SEPARATE AND ALTERNATING RF SIGNALS

(71) Applicant: TEXAS INSTRUMENTS INCORPORATED, Dallas, TX (US)

(72) Inventor: Phillip Michel Nadeau, Cambridge, MA (US)

(73) Assignee: Texas Instruments Incorporated, Dallas, TX (US)

(*) Notice: Subject to any disclaimer, the term of this patent is extended or adjusted under 35 U.S.C. 154(b) by 445 days.

(21) Appl. No.: 13/900,668

(22) Filed: May 23, 2013

(65) Prior Publication Data

US 2014/0347074 A1 Nov. 27, 2014

(51) Int. Cl.
*G01N 22/00* (2006.01)
*G01R 27/28* (2006.01)

(52) U.S. Cl.
CPC .............. *G01N 22/00* (2013.01); *G01R 27/28* (2013.01)

(58) Field of Classification Search
CPC ............... G01N 22/00; G01N 2201/0694; G01N 2201/1211; G01N 2201/1247; G01S 7/02; G01S 7/40; G01S 7/4008; G01S 7/4021; G01S 7/41; G01S 7/411; G01S 7/412; G01S 7/48; G01S 7/4802; G01S 7/497; G01S 13/02; G01S 13/88; G01S 3/1303; G01S 17/026; G01S 3/0304; G01J 3/00; G01J 3/02; G01J 3/28; G01J 3/42; H01S 5/0687; H01S 5/0654; H01S 5/1392; F16P 3/14; F16P 3/142; F16P 3/144; F21V 23/0442; F21V 23/045; F21V 23/0457; F21V 23/0471; F21V 23/0478; F21V 23/0485; G01V 8/10; G06F 3/0304; G06F 3/0308; G06F 3/0312; G06F 3/0317; G06F 3/0321; G06F 3/042

USPC ..................... 324/76.11, 76.12, 76.13, 76.14, 324/76.19–76.39, 633, 636, 600, 629, 637, 324/639, 642; 342/22, 89–90, 165–175, 342/192–197, 350, 351; 73/1.01, 1.02, 73/1.06, 23.2; 356/300, 326, 51, 302, 303, 356/311, 316, 450, 451, 454; 250/253, 256, 250/269.1, 269.6, 269.8, 281, 282, 200, 250/216, 221

See application file for complete search history.

(56) References Cited

U.S. PATENT DOCUMENTS

| | | | |
|---|---|---|---|
| 2,728,855 A * | 12/1955 | Norton | 324/76.66 |
| 4,972,699 A * | 11/1990 | Berger et al. | 324/639 |
| 7,057,398 B2 * | 6/2006 | Zhu et al. | 324/639 |
| 2013/0321815 A1 * | 12/2013 | Otera | 356/437 |
| 2014/0368376 A1 * | 12/2014 | Nadeau et al. | 342/174 |
| 2014/0368377 A1 * | 12/2014 | Nadeau et al. | 342/192 |

(Continued)

*Primary Examiner* — Melissa Koval
*Assistant Examiner* — Felicia Farrow
(74) *Attorney, Agent, or Firm* — Lawrence J. Bassuk; Frank D. Cimino

(57) ABSTRACT

A method to detect a gas absorption line that includes alternately transmitting and sweeping two radio frequency (RF) signals through an absorption cell, wherein the two RF signals are transmitted at different frequencies separated by a range and are swept across a span of frequencies in a microwave and millimeter wave regions of a frequency spectrum. Receiving the RF signals by a receiver and analyzing the received signals by a closed loop system for relative absorption by a gas due to an absorption line of the gas in the span of the swept frequencies. Detecting the absorption line of the gas when the two RF signals straddle the gas absorption line and the relative absorption by the two RF signals is equal.

12 Claims, 2 Drawing Sheets

DETERMINING GAS ABSORPTION LINE FROM SEPARATE AND ALTERNATING RF SIGNALS

BACKGROUND

Spectroscopy and spectrometers may be used as various measurement and reference tools. They may use an array of measurement techniques on just about any form of matter. The measurement techniques may depend on the material of interest, which may dictate what frequency/wavelength may be best suited for the measurements. Spectrometers, for example, may be suited to measure emission or absorption spectrums. Further, absorption spectrometers may specifically look for characteristic absorption lines of the material. The absorption lines may be used to identify an unknown substance from a catalogue of known spectrums, or it may be used to detect the amount of that known substance in a sample. In general, spectroscopy principles may be used for various measurements or to define a reference based on frequency or wavelength.

SUMMARY

A method, device and system for detecting and tracking the center frequency of an absorption line is described herein. One embodiment is a method that includes alternately transmitting and sweeping two radio frequency (RF) signals through an absorption cell, wherein the two RF signals are transmitted at different frequencies separated by a range and are swept across a span of frequencies in a microwave and millimeter wave regions of a frequency spectrum. Receiving the RF signals by a receiver and analyzing the received signals by a closed loop system for relative absorption by a gas due to an absorption line of the gas in the span of the swept frequencies. Detecting the absorption line of the gas when the two RF signals straddle the gas absorption line and the relative absorption by the two RF signals is equal.

Another embodiment includes a system for detecting an absorption line of a gas that includes a processor, a signal generator coupled to the processor, a transmitter coupled to the signal generator configured to generate two radio frequency (RF) signals. Each RF signal generated at a different frequency and are separated by a set frequency range. The two RF signals are alternately transmitted, and are swept across a span of frequencies in a microwave and millimeter wave region of a spectrum to detect an absorption line of the gas. A receiver coupled to the processor, an absorption cell filled with a gas at a pressure, wherein the transmitter transmits the two RF signals through the absorption cell and the two RF signals are detected by the receiver. And a detector module to compare the amplitudes of the two received RF signals and to determine when an absorption line of a gas is detected based on a difference in the amplitudes between the two RF signals.

Yet another embodiment is a gas absorption line detecting and tracking device that includes an absorption cell filled with a gas, a transmitter to transmit RF signals through the absorption cell, a receiver to receive the RF signals, and a control module coupled to the transmitter and the receiver to detect an absorption line of the gas using a frequency-shift keying (FSK) detection scheme operating in a microwave and a millimeter wave frequency region of a spectrum.

BRIEF DESCRIPTION OF THE DRAWINGS

For a detailed description of exemplary embodiments of the invention, reference will now be made to the accompanying drawings in which.

NOTATION AND NOMENCLATURE

Figure 1:
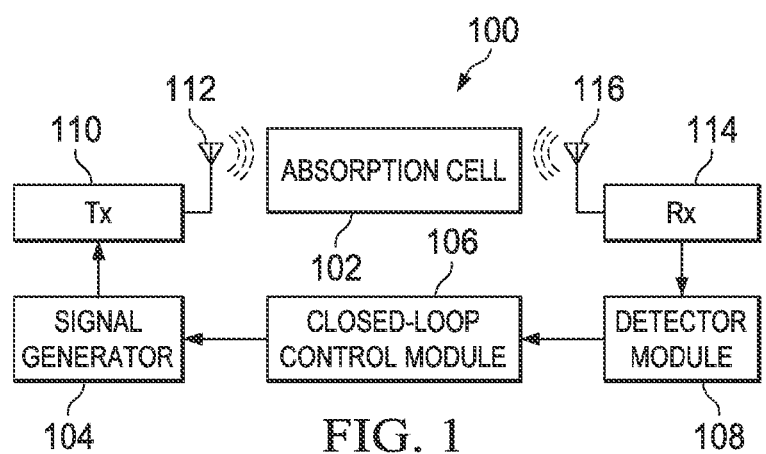
FIG. 1 shows a block diagram of a spectrometer which may be used for the detection and tracking of a gas absorption line in accordance with various embodiments described herein.

Certain terms are used throughout the following description and claims to refer to particular system components. As one skilled in the art will appreciate, companies may refer to a component by different names. This document does not intend to distinguish between components that differ in name but not function. In the following discussion and in the claims, the terms "including" and "comprising" are used in an open-ended fashion, and thus should be interpreted to mean "including, but not limited to . . . " Also, the term "couple" or "couples" is intended to mean either an indirect or direct electrical connection. Thus, if a first device couples to a second device; that connection may be through a direct or indirect connection.

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Conventional spectrometers utilize a wide array of probing and measurement techniques depending on the material being measured and the characteristic(s) of interest. As used herein, "probing" may mean a radiation signal impinging on or transmitted through the material being measured. It is the interaction of the material being measured with the probe signal that may produce the measured spectrum. As such, spectrometers may be designed to detect and measure reflection, transmission, or excitation, to name a few examples. Additionally, a single material may have different mechanisms excited and observed at different frequencies within different frequency ranges. For example, a gas may display absorption due to the excitation of vibrational states of the gas in one frequency range and then display absorption at a different range of frequencies associated with rotational excitation. Electron excitation within the gas molecules may occur at a third range of frequencies. In short, depending on what aspect of a material is desired to be studied and measured, different excitation and measurement mechanisms may be used.

Spectroscopy utilizes radiation energy to probe the material being measured. For example, to measure the absorption spectrum of air, electro-magnetic (EM) radiation at different frequencies in the form of radio-frequency (RF) signals may be transmitted through a sample of air in a gas cell. The transmitted signal may be detected and measured after the RF signals exit the cell. The resulting spectrum may display different absorption/transmission characteristics of the air for the frequencies transmitted, or measured. Further, the RF signals may be modulated before transmission to aid in their detection. Modulation schemes may include amplitude modulation (AM), frequency modulation (FM), and frequency-shift keying (FSK), to give a few examples. As noted, the modulation scheme may help detect the signal from noise or any background radiation at those frequencies.

In the case of absorption spectroscopy, the measured signal may show a decrease in magnitude compared to the transmitted signal with the decrease in magnitude representing the amount of absorption by the gas at that frequency. As such, an absorption spectrum over a series of frequencies may show different absorption characteristics at various frequencies within that series that correlate to a rotational or vibrational excitation state, or, in other words, an absorption line of the material. Because the absorption lines correlate to a physical excitation of the material, the center frequency of that excitation should remain roughly constant, with only minor shifts due to pressure and temperature changes.

The shape of the absorption line, however, may vary due to environmental conditions of the sample. An ideal absorption line would be a delta function, but in reality, the absorption line has a width that covers a small range of frequencies. The width of the range, or the width of the absorption line, may be due to the environmental factors, for example temperature or pressure. The width of the absorption line may indicate excess energy of the sample. At high pressures the absorption line may be very wide and difficult to discern from the rest of the measured spectrum. At very low pressures, there may not be enough gas in the cell to permit a reliable measurement. As such, a range of preferable pressures may give reliable, repeatable, measurements. Temperature changes may impart the same effects to the sample.

The measurement's reliability and repeatability may also be affected by the modulation scheme used by the spectrometer. The use of FM, AM or FSK modulation may create a more detectable signal at the detector due to the detector being tuned to those modulation schemes. Additionally, FSK, which uses two probing signals, may allow the spectrometer to more easily lock in on and track an absorption line of the material since the two signals may be positioned around the absorption line and a feedback mechanism used to vary the two signals as necessary so that they remain in the same positions with respect to the absorption line.

Disclosed herein are devices, systems and methods that detect and track an absorption fine of a gas in the millimeter-wave (mmwave), microwave, and/or terahertz (THz) regions of the EM spectrum. The detection and tracking of the absorption may use the FSK modulation scheme and a closed-loop control module that allows locking in on and tracking the center frequency of the absorption line. The closed-loop control module may use an error signal generated by the FSK modulation scheme as a factor in the control function of the module. Further, the two tones of the FSK scheme may be used to detect and track the 183.31 GHz absorption line of water.

FIG. 1 shows a block diagram of a spectrometer 100 which may be used for the detection and tracking of a gas absorption fine in accordance with various embodiments described herein. The spectrometer 100 may comprise an absorption cell 102 (the absorption cell 102 may also be referred to herein as the cell 102), a signal generator 104, a closed-loop control module 106, and a detector module 108. In addition, the spectrometer 100 may also comprise a transmitter 110 with an associated antenna 112 and a receiver 114 with an associated antenna 116. The transmitter 110 and the receiver 114, via their respective antennas 112,116, may be used to transmit and receive EM radiation energy in the mmwave, microwave and/or THz regions of the EM spectrum. As such, the transmitted signals may range in frequency from the low gigahertz range to the upper THz range.

The cell 102 may be filled with a gas at a pressure and may be of varying lengths. The pressure of the gas in the cell 102 may range from 0.01 mbar to 10 mbar. The length of the cell 102 may affect the signal-to-noise ratio of the received signal and may also affect the length of time the spectrometer 100 takes to detect and lock in on an absorption line of the gas. The absorption cell may include valves and pumps (not shown) so that the gas within the cell 102 may be changed and/or the pressure of the cell 102 may be adjusted to a desired level. The temperature of the cell 102 may also be adjustable (not shown). In accordance with various embodiments, the cell 102 may be filled with air at about 0.1 mbar of pressure.

Figure 2A:
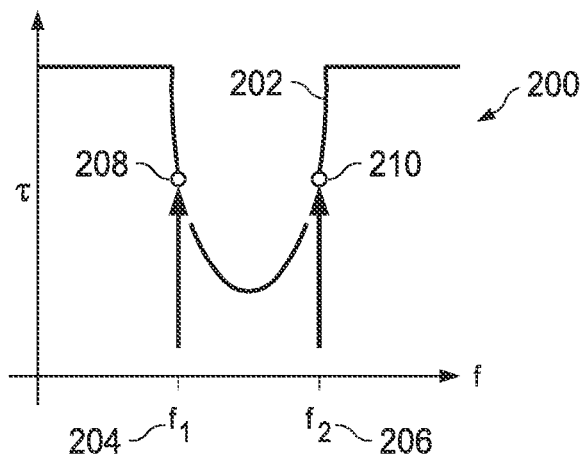
FIG. 2A is a representative plot of a transmission spectrum 200 including two tones used for measuring the spectrum 200.

FIG. 2A is a representative plot of an absorption spectrum 200 including two tones used for measuring the spectrum 200 of the gas in the cell 102. The absorption spectrum 200 shows an absorption line 202 and two RF signals or tones—f1 204 and f2 206. The x-axis of the absorption spectrum 200 may be in units of frequency (Hz), wavelength, or wavenumber and the y-axis may be in units of magnitude representing the signal strength and may be in volts or relative transmission (percentage, dB, or unitless). The signal generator 104 may alternately generate the two tones 204 and 206, separated by a set frequency range, e.g. less than 1 MHZ. Alternatively, the range separating the two tones 204, 206 may be set equal to the bandwidth of the absorption line of interest or to the point of maximum slope of the absorption line as is shown in FIG. 2A at points 208 and 210. Setting the range separating the two tones to intersect with the absorption line at the point of maximum slope, points 208, 210 in FIG. 2A, may assist with increasing the signal-to-noise ratio in the measured signal and may allow for faster tracking of the absorption line. The two tones 204, 206 may be swept across a span of frequencies in lock step while keeping the range separating them constant. Further, the frequencies at which the two tones 204, 206 are generated may be alternated between at a 50% duty cycle so that each tone is generated separately. The two tones 204, 206 generated by the signal generator 104 may be transmitted by the transmitter 110/antenna 112 combination into and through the cell 102.

The receiver 114, via the antenna 116, receives the transmitted tones 204, 206 after they have passed through the cell 102. The receiver 114 communicates the received signals to the detector module 108. The detector module 108 may generate a square wave out of the two received tones. The square wave may represent the relative absorption of the two tones by the gas in the cell 102.

Figure 2B:
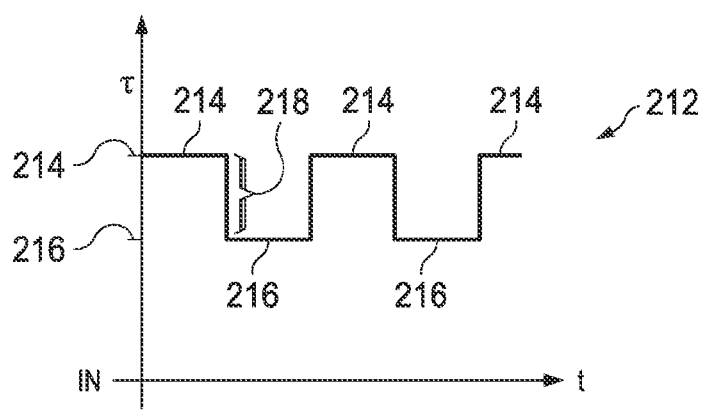
FIG. 2B is a representative plot of a square wave 212 received by a detector from the two received FSK tones which have been modulated by the gas' transmission spectrum.

FIG. 2B is a representative plot of a square wave 212 generated by the detector module 108 from the two received FSK tones. The square wave 212 comprises two signal levels 214 and 216, with the signal levels representing the magnitude of the received signals, and an offset 218. The x-axis of the square wave 212 may be in units of time and the y-axis may be in arbitrary units of magnitude, voltage or relative absorption. Signal level 214 may correspond to the received signal 208 while signal level 216 corresponds to the received signal 206, or the correspondence may be reversed. A square wave 212 may be produced by the detector module 108 due to the two tones 204, 206 experiencing different amounts of absorption by the gas in the cell 102. When the two signals are absorbed by different amounts the offset 218 is produced in the square wave. In other words, the square wave 212, and more specifically the offset 218, may represent and may be proportional to the difference along the frequency axis the two tones 204, 206 are from the center frequency of the absorption line 202. Or, the offset represents how far the middle point of the range separating the two tones is from the center frequency of the absorption line 202. As such, the two tones 204, 206 may straddle the absorption line 202 when the square wave 212 becomes a straight line. In other words, the center frequency of the absorption line 202 has been found when the offset 218 becomes zero.

Further, the received signals detected by the detector module 108 may provide information about the absorption characteristics of the gas over the span of frequencies in which the two tones were swept. This information, the offset corresponding to a range of frequencies around the absorption line 202, may be used by the closed-loop control module 106 to lock-in on and track the center frequency of the absorption line. The offset 218, being the error signal, may be used to drive an integrator control loop. The detector module 108 may generate a table of the offset 218 values for a range of frequencies around the absorption line in question. The table of offset 218 values may be used to generate a plot that may be used by the close-loop control module 106 to further define additional parameters of the integrator control loop.

Although the detector module 108 may generate offset 218 range information to assist in defining certain feedback control parameters, the generation of the offset range information may not be necessary to the operation of the spectrometer 100 and are discussed for illustration purposes. The property that the offset 218 is linearly proportional to the frequency difference (and ideally zero when the absorption line frequency and the center of the two tones 204, 206 coincide) is all that may be required for the error signal. Still, determining the slope of the generated plot may help to decide the optimal control parameters, namely the inverse of the slope, to obtain the fastest possible response with minimal ringing, though this is not strictly required.

Figure 2C:
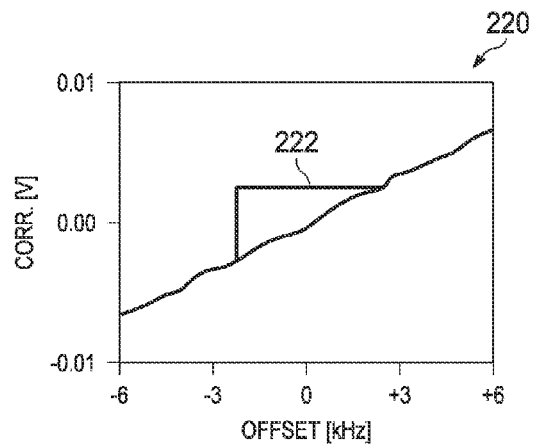
FIG. 2C is a representative offset plot 220 of the lock-in amplitude at various frequencies very near to the absorption line of a gas.

FIG. 2C is a representative offset plot 220 at various frequencies around the absorption line of a gas. The offset plot 220 has values of frequency (Hz) for the x-axis and values of voltage for the y-axis. The slope 222 of the offset plot 220 corresponds to the change in offset 218 when the two tones 204, 206 are at different frequencies with respect to the center frequency of the absorption line but are still straddling the absorption line at various degrees. The slope 222 represents a change in volts per frequency and may be used by the closed-loop control module 106 to aid in detection, locking-in on, and tracking the absorption line 202.

The closed-loop control module 106 may use the error signal to drive the signal generator 104 to lock-in on and track the absorption line of interest, once the absorption line is detected. The error signal may reduce to zero once the two tones 204, 206 exactly straddle the absorption line. However, if the two tones 204, 206 begin to drift up or down the frequency spectrum, then the error signal may change positively or negatively. The change in the error signal may cause the closed-loop control module to adjust the frequencies of the two tones 204, 206 generated by the signal generator 104.

Figure 3:
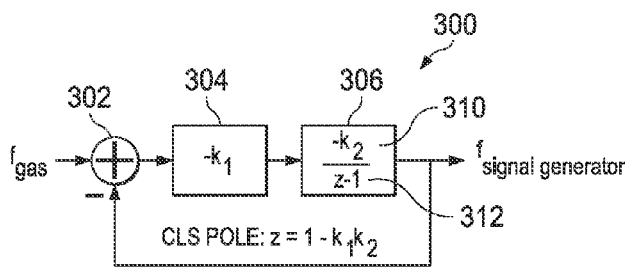
FIG. 3 shows a block diagram of a closed loop control function 300 implemented by the spectrometer 100 in accordance with various examples described herein.

The closed-loop control module 106 may implement an integrator control loop that incorporates the error signal and the inverse of the error signal slope (vs. frequency offset) as factors in the control loop transfer function. FIG. 3 shows a block diagram of a closed loop control function 300 implemented by the closed-loop control module 106 of the spectrometer 100 in accordance with various examples described herein. The control function 300 may comprise an adder block 302, a multiplier block 304, and a second multiplier block 306. The adder block 302 generates an error amount between two signals $f_{gas}$ and $f_{signal\ generator}$. The error amount is then multiplied by a conversion factor in block 304 that converts frequency to voltage. The resulting error amount in units of voltage is then multiplied by block 306 that drives the response time of the closed-loop control module 106.

The input to the control function may be the ideal center frequency of the absorption line being measured, denoted as $f_{gas}$ in FIG. 3, and may be used as a reference by the closed-loop control module 106. The output of the control function may be the estimate of the center frequency of the absorption line, denoted as $f_{signal\ generator}$ in FIG. 3, and may be used to drive the signal generator 104. The frequency $f_{signal\ generator}$ may be the mid-point frequency between the two tones 204, 206, which would be used to determine the frequency that each of the two tones should be driven. The k1 304 may be the slope of the error response given a frequency offset in Hz that is generated by the detector module 108 and the k2 310 may be the inverse of the k1 304. By choosing the k2 310 as the inverse of k1 304, the closed-loop discrete pole, z 312, may be driven to zero, which may produce the fastest response time for locking in on the absorption line by the spectrometer 100.

The closed-bop control module 106 may then control the signal generator 104 to continuously change the frequencies at which the two tones are transmitted so that the center frequency of the absorption cell is tracked. By tracking the center frequency of the absorption line, the spectrometer 100 may provide a frequency reference with parts-per-billion frequency accuracy.

FIG. 1 depicts several separate elements comprising the spectrometer 100. However, it will be appreciated that multiple dements may be combined. For example, the signal generator 104, the closed-loop control module 106, and the detector module 108 may be combined into a single device, such as a detection and control module. Alternatively, some of the pieces may be implemented as software being executed by a computer or digital signal processor or as a combination of hardware and software.

Figure 4:
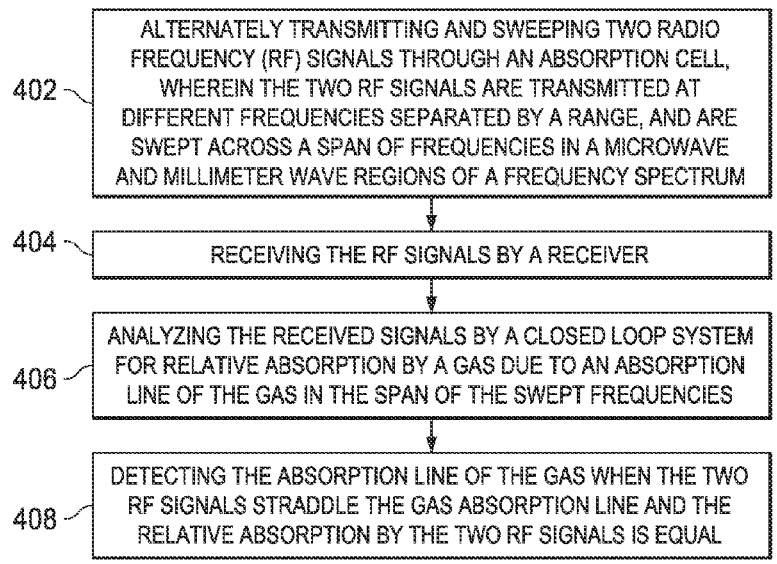
FIG. 4 shows a flow chart for a method to implement the detection and tracking of a gas absorption line in accordance with various embodiments described herein.

FIG. 4 shows a flow chart for a method 400 to implement the detection and tracking of a gas absorption line in accordance with various embodiments described herein. The method 400 begins at block 402 with alternately transmitting and sweeping two RF signals through an absorption cell. The two RF signals are transmitted at different frequencies separated by a range, and are swept across a span of frequencies in a microwave and millimeter wave regions of a frequency spectrum. The frequencies of the two tones may be transmitted at a 50% duty cycle so that only one of the two tones is transmitted at a time. The two RF signals, or tones, are similar to the two tones 204, 206 described above and may be transmitted and swept across the span of frequencies by the signal generator 104.

The block 404 of the method 400 includes receiving the RF signals by a receiver. The two RF signals, or tones, may be received by the receiver 114/antenna 116 combination as described above. The receiver 114 may then communicate the received signals to the detector module 108 where analysis of the signals may be carried out by the detector module 108.

The block 406 of the method 400 includes analyzing the received signals by a closed-loop system for relative absorption by a gas due to an absorption line of the gas in the span of the swept frequencies. The closed-loop system may be the combination of the detector module 108 and the closed-loop control module 106. Alternatively, the closed-loop system may further comprise the signal generator 104. The analysis of the received signals may follow the analysis performed by the detector module 106 described above. The two received signals will be used to generate a square wave that will inform the closed-loop system of the relative frequency relationship between the two tones and the absorption line of the gas. The levels of the square wave may represent the relative absorption of the transmitted signals by the gas. The square wave may be detected via lock-in techniques to help improve the signal to noise ratio and reduce the acquisition time.

The block 408 of the method 400 includes detecting the absorption line of the gas when the two RF signals straddle the gas absorption line and the relative absorption by the two RF signals is equal. As described above, the gas absorption line, and more precisely the center frequency of the absorption line, is detected when the relative absorption by the two RF signals, tones, is equal. Being equal is similar to when the square wave described above becomes a straight line and the offset 218 becomes zero. When the offset 218 becomes zero, the two tones may exactly straddle the center frequency of the absorption line.

Additionally, the method 400 may further comprise tracking the absorption line of the gas by the closed-loop system. The center frequency of the absorption may be maintained in the middle of the range of frequencies separating the two RF signals. Tracking may be implemented by using the offset 218 as an error signal to the closed-loop control module 106. Implementing the closed-loop control utilizing the error signal may allow the absorption line to be tracked using the relative absorption of the two RF signals by the gas in the cell 102.

The order the method 400 is described is not dispositive of how the method may be implemented. Steps of the method 400 may be carried out in a different order than presented or steps may be combined and carried out simultaneously. Alternatively, many, if not all, of the steps of the method 400 may be performed in parallel. One of ordinary skill in the art would appreciate the variations in performing the described method to produce the desired outcome.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:

1. A method to detect a gas absorption line, comprising:
   transmitting and sweeping two separate and alternating radio frequency (RF) signals from a signal generator through an absorption cell containing a gas, including transmitting the two alternating RF signals at different frequencies separated by a constant range, and including sweeping the two alternating RF signals across a span of frequencies in microwave and millimeter wave and THz regions of a frequency spectrum;
   receiving the RF signals from the absorption cell by a receiver;
   analyzing the received RF signals by a closed loop system for relative absorption by the gas due to an absorption line of the gas in the span of the swept frequencies; and
   detecting the absorption line of the gas when the two received RF signals straddle the gas absorption line and the relative absorption by the two received RF signals is equal.

2. The method of claim 1, further comprising tracking the absorption line of the gas by the closed loop system, wherein the center frequency of the absorption line will be maintained in the middle of the range separating the two RF signals and the gas absorption line is tracked using the relative absorption between the two RF signals.

3. The method of claim 1, further comprising:
   generating an offset based on the relative absorption between the two RF signals; and
   applying the offset as an error signal in the closed loop system.

4. The method of claim 3, further comprising:
   inverting the offset slope; and
   applying the inverted offset slope as another in the closed loop system.

5. The method of claim 1, wherein detecting the absorption line comprises using frequency-shift keying as a detection scheme.

6. A system for detecting an absorption line of a gas, comprising:
   a signal generator having a transmitter output and a control input, the signal generator, in response to the control input, generating two radio frequency (RF) signals, each at a different frequency, the two RF signals are separated by a constant frequency range, are alternately transmitted, and are swept across a span of frequencies in a microwave and millimeter wave region of a spectrum;
   an absorption cell filled with the gas at a pressure;
   a transmitter coupled to the output of the signal generator and transmitting the RF signals into the absorption cell;
   a receiver receiving absorption RF signals from the absorption cell; and
   a processor having an output coupled to the input of the signal generator and including a detector module having an input coupled to the receiver to compare the amplitudes of the two received absorption RF signals and to determine when an absorption line of a gas is detected based on a difference in the amplitudes between the two RF signals.

7. The system of claim 6, further comprising: a closed-loop control module to lock-in the detection of the gas absorption line using the difference between the absorption of the two RF signals by the gas as a factor in a closed-loop control algorithm.

8. The system of claim 7, wherein the inverse of the offset slope between the absorption of the two RF signals by the gas is a factor in the closed-loop control algorithm.

9. The system of claim 6, wherein the absorption cell is filled with air at 0.1 mbar.

10. The system of claim 6, wherein a 183.31 GHz absorption line of water is the absorption line of the gas.

11. The system of claim 6, wherein the constant frequency range is less than 1 MHz.

12. The system of claim 6, wherein a frequency-key shifting scheme is used by the detector module.

* * * * *